United States Patent
Lin et al.

(10) Patent No.: US 6,246,907 B1
(45) Date of Patent: Jun. 12, 2001

(54) AUTOMATIC EXTERNAL CARDIOVERTER/ DEFIBRILLATOR WITH CARDIAC RATE DETECTOR AND METHOD OF OPERATING THE SAME

(75) Inventors: Dongping Lin, Irvine; Raul Ybarra, Newhall; Prabodh Mathur, Laguna Niguel, all of CA (US)

(73) Assignee: CardiacScience, Inc., Irvine, CA (US)

( * ) Notice: Subject to any disclaimer, the term of this patent is extended or adjusted under 35 U.S.C. 154(b) by 0 days.

(21) Appl. No.: 09/452,496

(22) Filed: Dec. 1, 1999

(51) Int. Cl.[7] ........................................ A61N 1/39
(52) U.S. Cl. ........................ 607/5; 600/519; 600/518
(58) Field of Search ..................... 607/5; 600/509, 600/515, 518, 519; 128/901

(56) References Cited

U.S. PATENT DOCUMENTS 3,699,949 * 10/1972 O'Hanlon, Jr. et al. ............. 600/519
5,405,362 * 4/1995 Krammer et al. ........................ 607/5
5,507,778 * 4/1996 Freeman .................................. 607/5
5,558,098 * 9/1996 Fain ........................................ 607/5
5,871,509 * 2/1999 Noren ..................................... 607/9

* cited by examiner

Primary Examiner—Kennedy Schaetzle
(74) Attorney, Agent, or Firm—Gottlieb, Rackman & Reisman, P.C.

(57) ABSTRACT

An external defibrillator includes a detector used to detect a life threatening condition of a patient, a controller operating the defibrillator automatically and a therapy delivery circuit that delivers appropriate therapy. The defibrillator is attached to a patient and is adapted to monitor the patient and when a life threatening condition is detected, to apply therapy automatically. An averaging scheme is used to determine a current cardiac rate by taking a first average of the intervals between a preset number of successive cardiac events, establishing a differential between this average and the intervals, dropping the interval corresponding to the largest differential. In this manner, the effects of over- and undersensing are eliminated or at least reduced.

34 Claims, 14 Drawing Sheets

AUTOMATIC EXTERNAL CARDIOVERTER/ DEFIBRILLATOR WITH CARDIAC RATE DETECTOR AND METHOD OF OPERATING THE SAME

BACKGROUND OF THE INVENTION

A. Field of Invention

This invention pertains to an external defibrillator arranged and constructed to provide anti-tachyarrhythmia therapy to a patient on demand. In particular, an automatic external cardioverter/defibrillator is described which has several operational modes including a fully automatic mode in which shocks are delivered without any manual intervention, an advisory mode and a manual mode. Moreover, the invention pertains to a defibrillator with an integral tachyarrhythmia detector which detects an abnormal heart beat and determines whether this abnormal heart beat is amenable to shock therapy.

B. Description of the Prior Art

Defibrillators are devices which apply electric therapy to cardiac patients having an abnormally high heart rhythm. Two kinds of defibrillators are presently available: internal defibrillators which are implanted subcutaneously in a patient together with leads extending through the veins into the cardiac chambers, and external defibrillators which are attached (usually temporarily) to the patient. External defibrillators are used in most instances in case of an emergency, for example, when a patient has either suffered cardiac arrest or where a cardiac arrest is imminent. Typically therefore external defibrillators are manual devices which must be triggered by a physician or other trained personal. Internal or implantable defibrillators (and cardioverters) are implanted as a permanent solution for patients having specific well defined cardiac deficiencies which cannot be treated successfully by other means. They generally operate in an automatic mode.

However, there are some instances where an external defibrillator would be very advantageous which could be operated in both automatic and manual modes. For example, presently, it is well known that after a cardiac episode, such as a sudden cardiac arrest, many patients frequently suffer a second episode of similar nature. Therefore, cardiac patients are kept in a hospital under observation. While in the hospital, the patient is attached to a monitor which indicates the patient's heart rate, temperature, respiration rate and other vital signs. Many monitors are provided with an alarm function which is activated when these vital signs fall outside a nominal range. The monitor then generates an audible and visual signal at the bed side of the patient and/or at the remote location such as a nurse station. However, if a cardiac episode does occur, the attending staff has to examine the patient to determine that the patient needs electrical therapy, and then set up and use a manual defibrillator. All these steps are inherently time-consuming.

Some attempt has been made to overcome some of these problems. For example, some external defibrillators are available which can verify that a patient is suffering from ventricular fibrillation VF and prompt an attendant to activate the defibrillator for the delivery of therapy. However, the algorithms used by these defibrillators to detect VF are very limited. For example, some of defibrillators utilize an algorithm in which the electrocardiogram ECG can be verified only while the patient is unconscious, has no pulse and does not breath. Obviously, these algorithms are not satisfactory since it is important to detect when those conditions happen and apply therapy as soon as those conditions are detected.

Commonly-owned U.S. Pat. No. 5,474,574 discloses an external defibrillator. Commonly-owned U.S. Pat. No. 4,576,170 discloses an external defibrillator that can be worn by a patient.

OBJECTIVES AND SUMMARY OF THE INVENTION

An objective of the present invention is to provide an automatic external cardioverter/defibrillator which is capable of detecting a current cardiac rate of a patient accurately by eliminating the effects of over- and under-sensing.

A further objective is to provide a defibrillator capable of performing amplitude and/or frequency analyses to detect a shockable rhythm based on a patient's ECG and to use the results of these analyses to categorize or recognize the current condition of the patient and to apply appropriate therapy for reverting the same.

Yet another objective is to provide an external defibrillator with several modes of operation, including an automatic mode in which shocks are applied on demand in accordance with preprogrammed shock parameters and without any prompting from an attendant, an advisory mode in which an attendant is alerted to a shockable rhythm however the application of shocks must be initiated by the attendant and a manual mode in which the attendant determines how and when shocks should be applied and the preprogrammed shock parameters are ignored.

Other objectives and advantages of the invention will become apparent from the following description of the invention.

DETAILED DESCRIPTION OF THE PREFERRED EMBODIMENT

Figure 1:
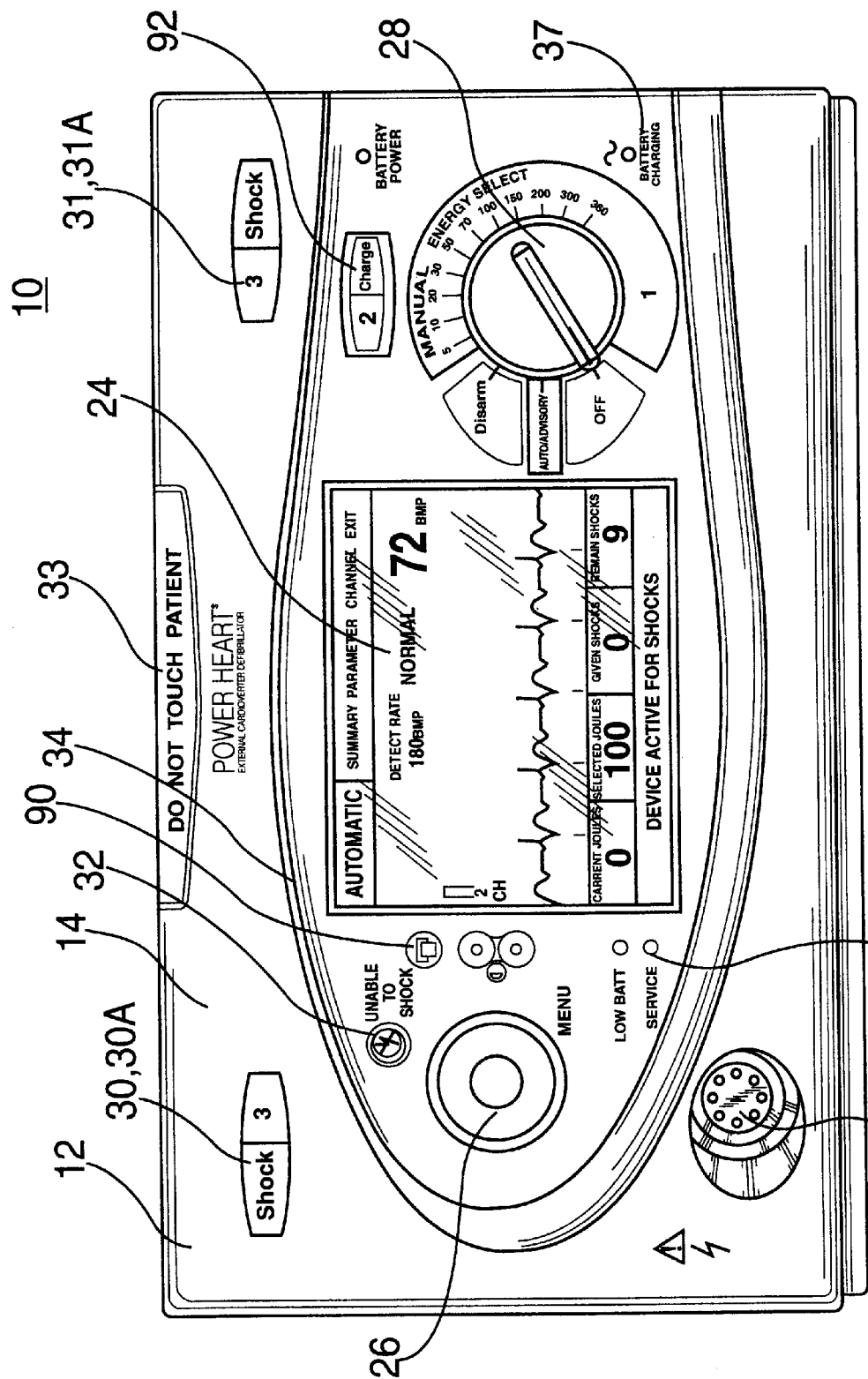
FIG. 1 shows a front view of an automatic external cardioverter/defibrillator constructed in accordance with the subject invention.
Figure 2:
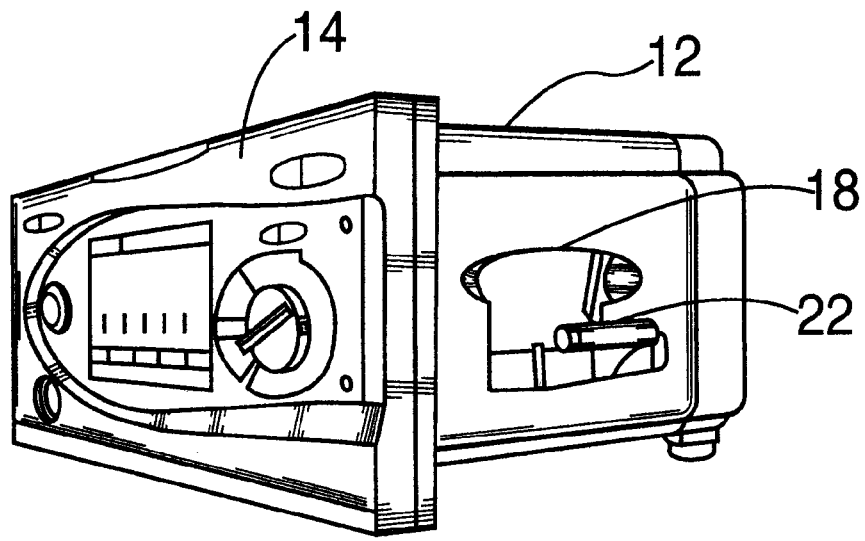
FIGS. 2 and 3 show an orthogonal view of the defibrillator of FIG. 1 with details of the printer on the side of the housing.
Figure 3:
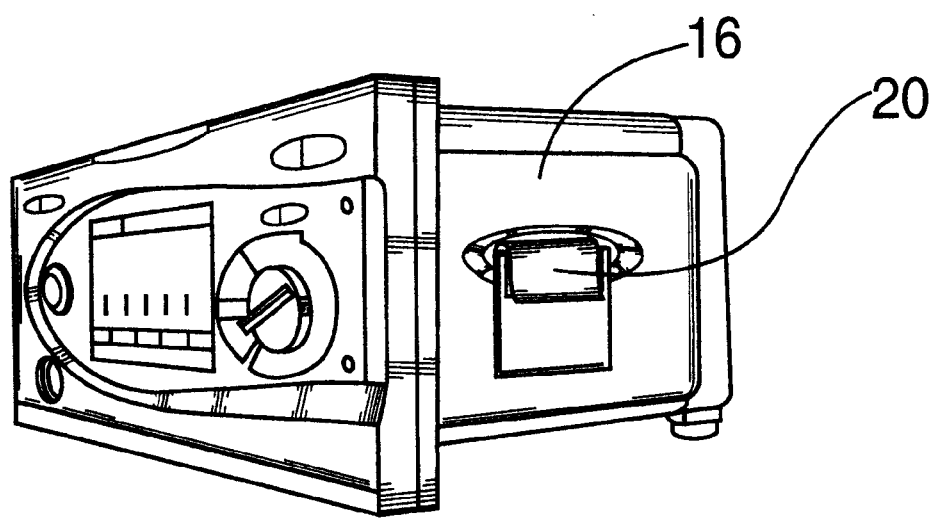

FIG. 1 shows a defibrillator 10 having a housing 12 with a front face display 14 on which a plurality of controls and indicating elements are provided, as described in more detail below. The defibrillator no further includes electrode assembly shown in FIG. 4 and described in detail below. As seen in FIGS. 2 and 3, one side 16 of the housing 12 is provided with a cavity 18. A printer (not shown) is mounted in cavity 18. A roll of paper 20 is mounted on shaft 22 in a manner which allows the printer to print alphanumeric characters and graphics on paper 20.

The housing 12 can be positioned on a rack, or other support means so that it can be disposed adjacent to the patient.

Referring back to FIG. 1, a screen display 24 is mounted on the front face 14 so that it is clearly visible. The display is used to provide information to the clinician related to the operation of the defibrillator 10, the status of the patient, etc. Disposed around the display 24, there are other indicator and control elements, such as the menu selection control knob 26, selector knob 28, charge button 92, shock buttons 30, 31 with built-in lights 30A, 31A respectively, and indicator lights 32, 34 and 36.

The menu selection control knob 26 is used in combination with the display 24 to select various operational parameters or operations for the defibrillator 10.

The knob 28 has several positions defining modes of operation, such as: Off, Auto/advisory, Disarm and Energy Selections. In the Off position, the defibrillator is deactivated. In the auto/advisory position, the defibrillator monitors the patient and can apply shocks using a preselected therapy. In the disarm position, an internal capacitor (not shown) is discharged to ensure that the defibrillator does not apply a shock accidentally. Finally, in the energy selection position, the defibrillator may be used to apply a shock to a patient at the selected energy level.

Figure 4:
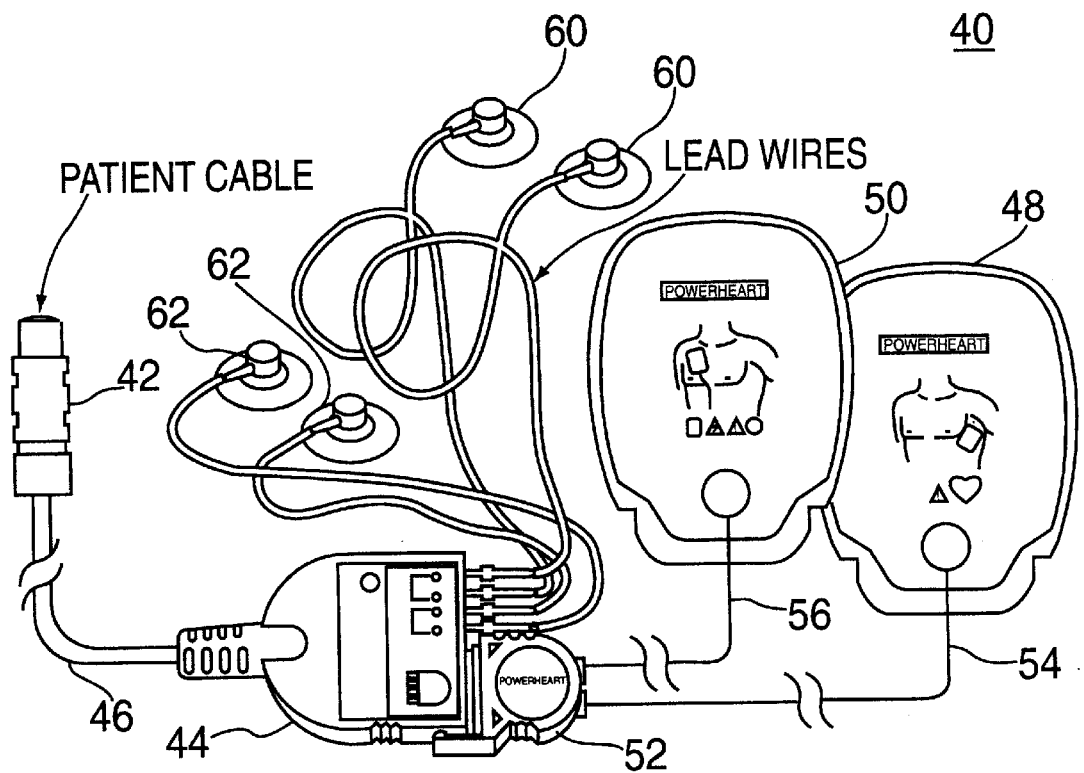
FIG. 4 shows the defibrillation and sensing electrodes used with the defibrillator of FIG. 1.

A socket 38 is provided for mating the housing 12 to the electrode assembly of FIG. 4. Near the top of the face 14, the housing 12 is provided with an additional illuminated indicator 33.

FIG. 4 shows details of the electrode assembly 40. The assembly 40 includes a first plug 42 constructed and arranged to mate with the jack 38 (FIG. 1), a connector 44 and a cable 46 extending between the plug 42 and the connector 44.

The assembly 40 further includes a pair of defibrillator pads 48 and 50 coupled to the connector 44 by an adapter 52, and two leads 54, 56 connected respectively to sensor electrode pairs 60 and 62. To ensure the defibrillation pads 48 and 50 are approved pads and they are used within their specified or approved time limit, e.g. 24 hours, a pad identification (pad ID) may be embedded in either the pads 48 and 58, cables 54, 56, and 46, or connectors 42 and 44. The defibrillator includes a capability to verify the pad ID and time it out after specified or approved time limit of usage.

Figure 5:
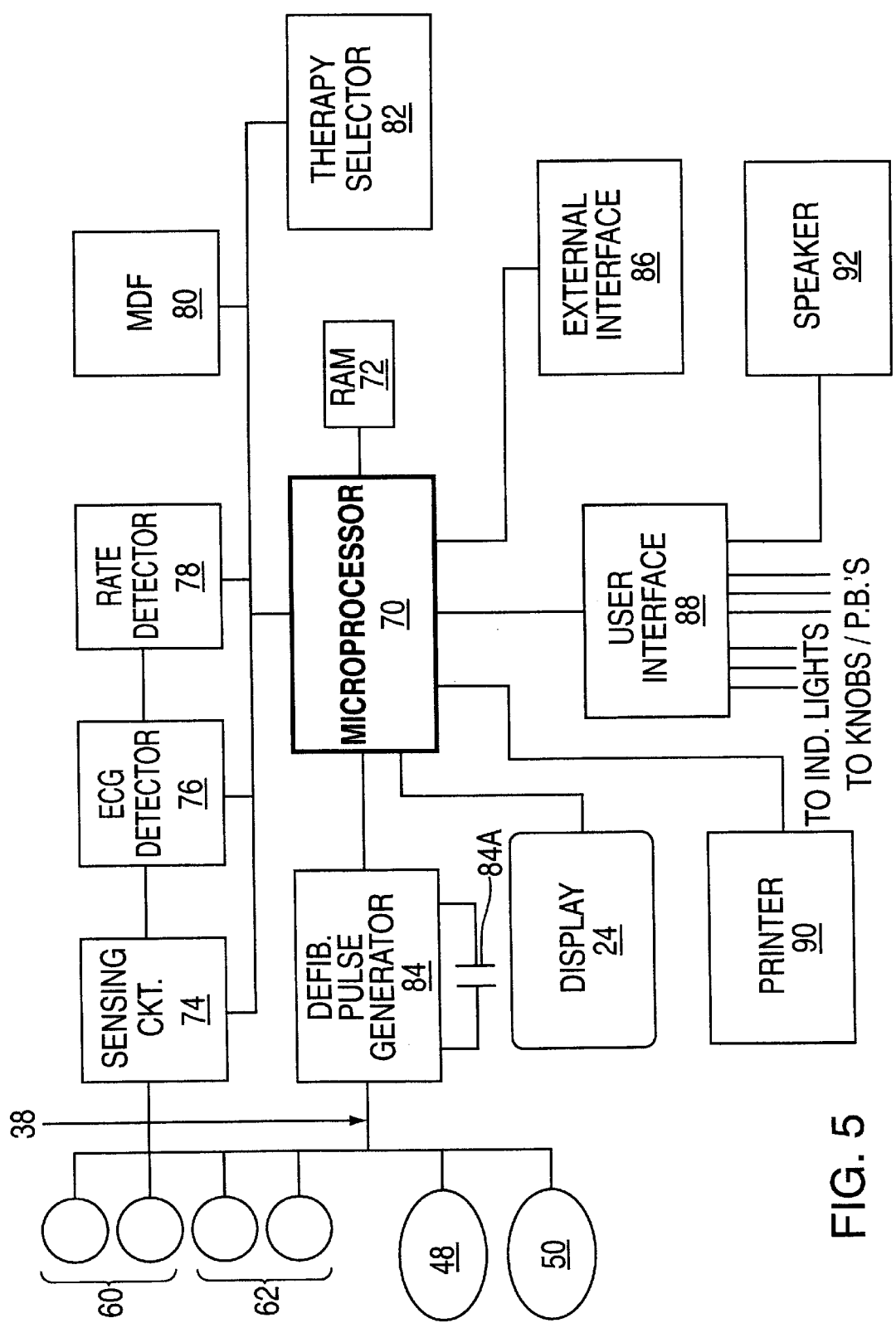
FIG. 5 shows a block diagram of the circuitry for the defibrillator of FIG. 1.

The defibrillator 10 also includes electronic circuitry disposed in housing 12 and used to operate the defibrillator and to generate the required electrical therapy. Referring to FIG. 5, the circuitry includes a microprocessor 70 which is associated with a memory 72 for storing programs and data logging information. The defibrillator further includes a sensing circuit 74, an ECG detecting circuit 76, a rate detector circuit 78, an MDF circuit 80, a therapy selector circuit 82, a defibrillator shock generator 84, an external interface 86, and a user interface 88. The microprocessor 70 receives commands from an attendant and other control signals through the various knobs, and push buttons shown in FIG. 1 via the analog interface 88. The microprocessor also activates various visual indicators and a speaker 92 through the same interface 88. The circuits shown in FIG. 5 can be implemented by software in RAM 72 however are shown as discrete circuits for the sake of clarity. Energy for the shocks is derived from a capacitor 84A associated with the generator 84.

As can be seen in FIG. 5, the electrode pairs 60, 62 and pads 48, 50 are connected through the jack 38 to a sensing circuit 74. This circuit 74 senses the intrinsic signals detected from the heart of the patient through the electrodes or pads, filters the same, converts them into digital signals at a sampling rate of, for example, 512 samples per second. Of course the filtering can be performed on the digital signals as well. The circuit 72 further includes an impedance measuring element (not shown) which measures the impedance of between the pads 48, 50. This impedance is provided to the microprocessor 70 so that the latter can determine if the pads and sensors are properly attached to the patient. The sensing circuit also detects if the sensing electrodes are connected properly.

The sampled digital signals from circuit 74 are fed to the microprocessor 70. The ECG detector circuit 76 and the rate detector circuit 78. The ECG detector 76 detects the ECG complex of the patient. The rate detector circuit 78 detects the current cardiac rate of the patient.

The microprocessor 70 analyzes the signals received from circuits 74, 76 and 78 and operates the other elements of defibrillator in accordance with these signals as discussed in more details below. In addition, the microprocessor 70 also sends information requested by an attendant to printer 80 when a pushbutton 90 (FIG. 1) is activated. In some cases, the microprocessor 70 activates the printer 80 automatically, for example, to display an ECG during defibrillation therapy.

The microprocessor can also exchange information with other devices or display a current ECG through an external interface 86.

Figure 7:
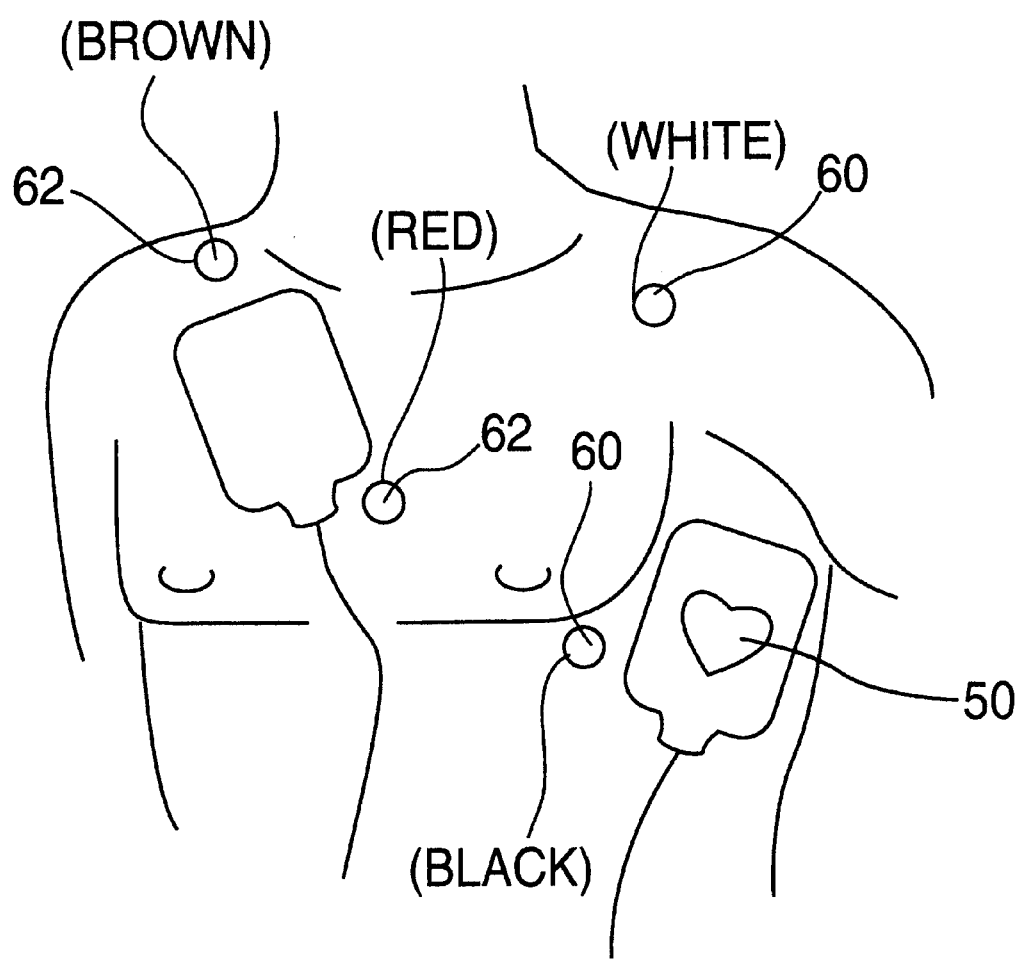
FIG. 7 shows diagrammatically the placement of the electrodes of FIG. 4 on a patient.

Before turning on the defibrillator 10, the pads 48, 50 and electrodes 60, 62 are positioned on the patient. FIG. 7 shows one possible positioning for these elements.

Figure 6:
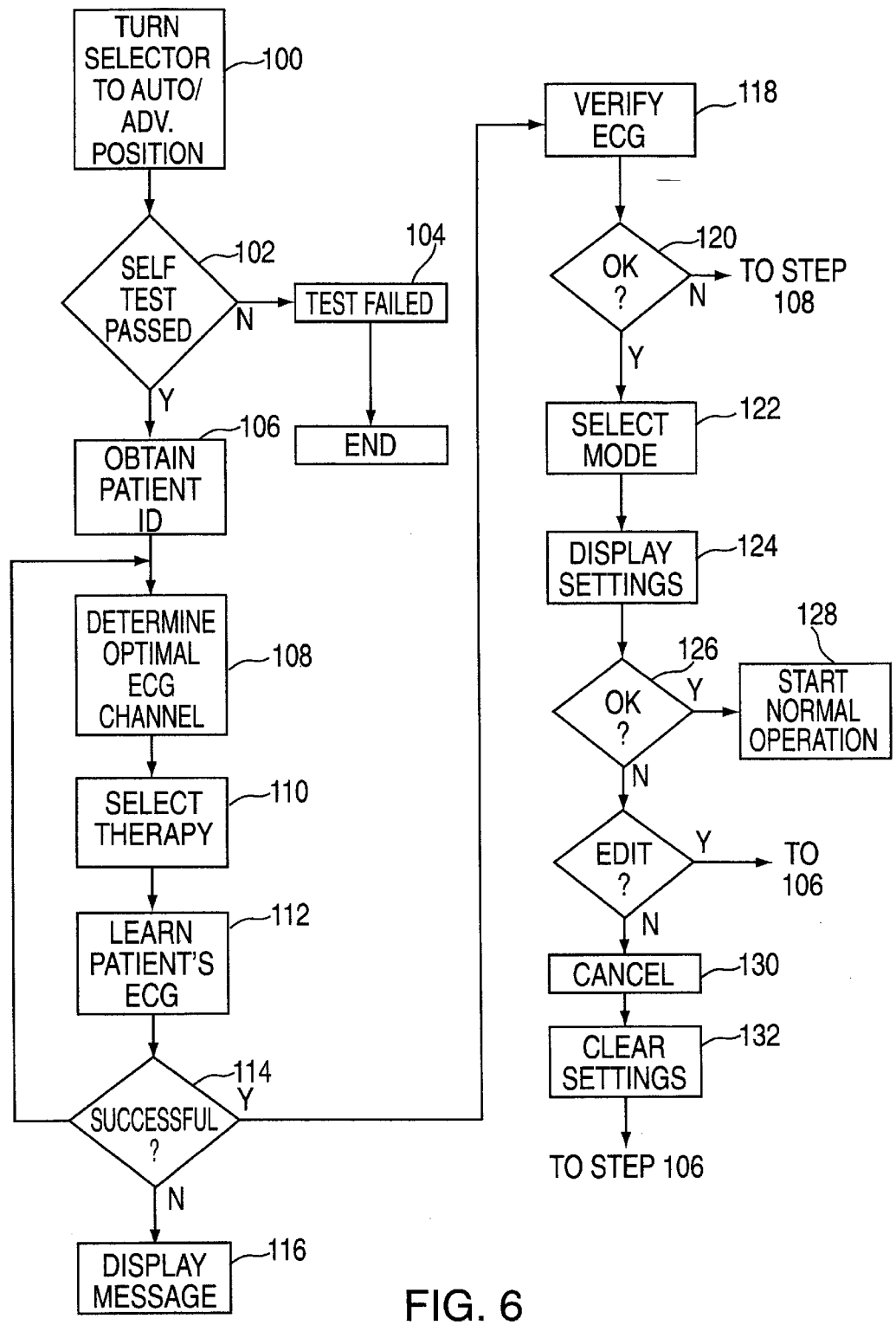
FIG. 6 shows a flow chart illustrating the steps required to initialize the defibrillator of FIG. 1.
Figure 9:
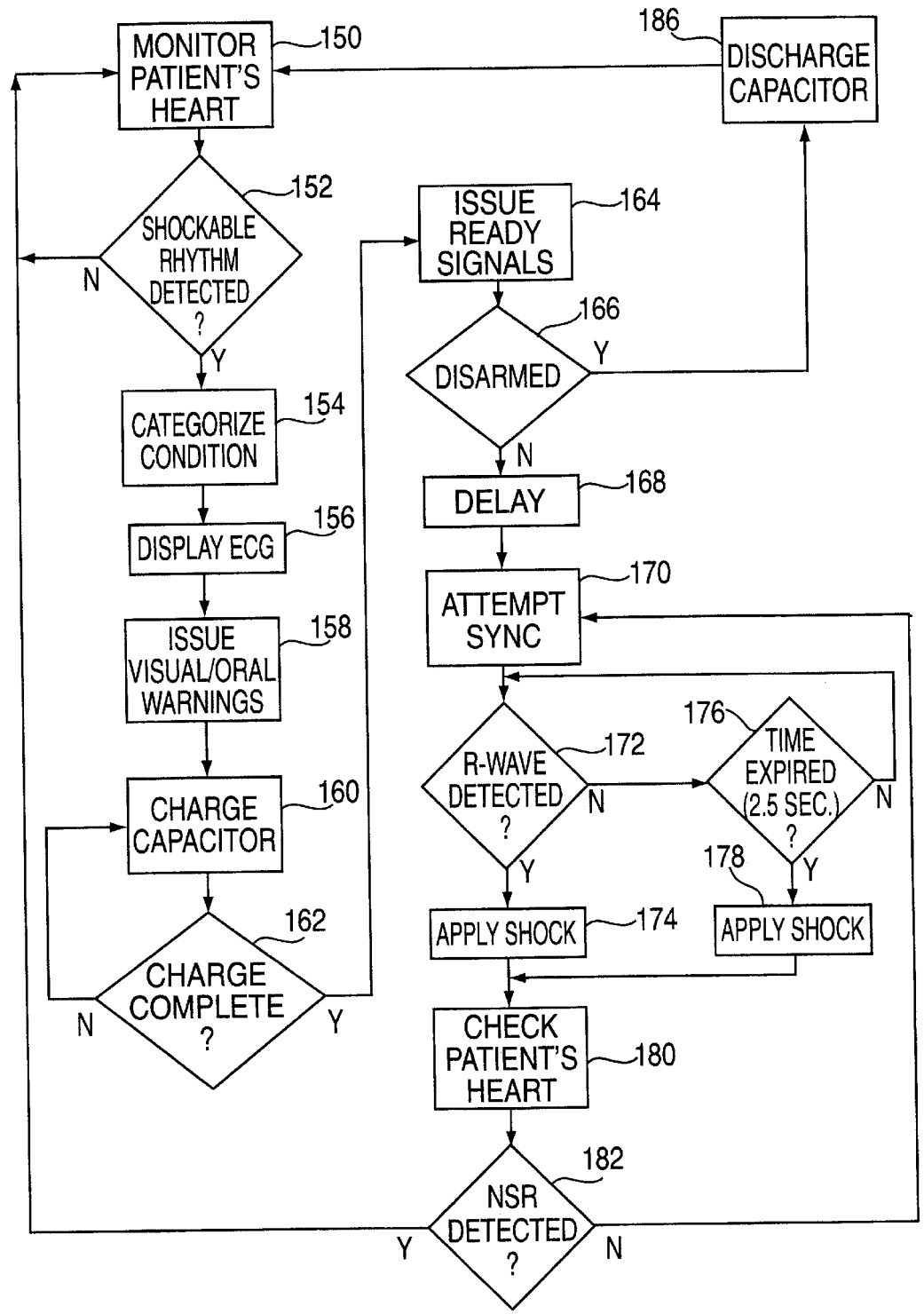
FIG. 9 shows a flow chart for the operation of the defibrillator of FIG. 1.

The operation of the defibrillator 10 and its microprocessor 70 is now described in conjunction with the flow charts of FIGS. 6 and 9. Before the defibrillator 10 can be operated, it must be initialized. This stage of initialization may be performed whenever the defibrillator 10 is set up for a particular patient. In one embodiment of the invention, the defibrillator 10 can be set up for only one patient at a time. In another embodiment, the defibrillator may be set up to provide therapy selectively to one of several patients, in which case, operational parameters unique for each patient are stored in its memory 88.

The first step in the initialization stage, step 100, the defibrillator 10 is turned on. This may be performed, for example, by turning the selector knob 28 to the auto/advisory position.

Once the defibrillator 10 is activated, it goes into a self-test mode (step 102) during which various internal functions and components are tested. During this step 102, the indicator light 32 illuminates to indicate that the defibrillator is currently unable to apply shocks and various sounds are emitted from the speaker (not shown) as well.

If the self-test fails in step 102, then in step 104, an error message is shown on display 24 and the initiation process is aborted.

If the self-test passes, then in the next step 106, the ID of the patient to be treated is obtained. For example, instructions may be shown on display 24 requesting the name and/or a unique number for the patient. The requested information can be entered by manipulating the knob 26 or by using a keyboard (not shown). The patient ID may be an optional field.

Next, in step 108, the ECG signals are analyzed to determine the best channel for the ECG acquisition. More particularly, the two pairs of sensing electrodes and the pads (which are also used in this instances as a sensing electrode pair) define three separate detection channels. The detection channel is selectable by an attendant.

Figure 8:
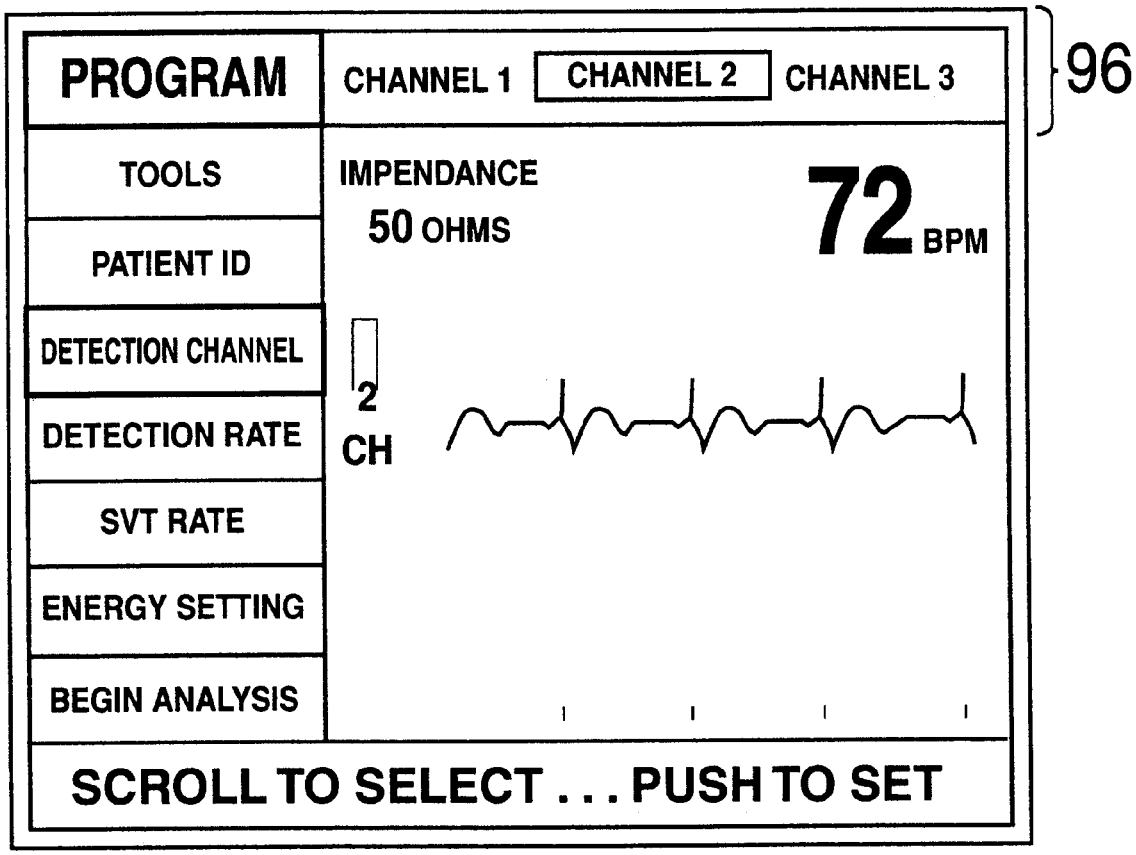
FIG. 8 shows a view of the display while an ECG is acquired during the initialization process of step 6.

Referring to FIG. 8, a portion 96 of display 24 identifies three detecting channels as channels 1, 2 and 3 respectively. In step 108, each of these channels is selected by manipulating knob 26. As each channel is selected, the ECG sensed through the corresponding pair of electrodes, the electrode pair impedance of the defibrillation pads, and current heart beat sensed through the electrodes is shown on the display 24. For example, in FIG. 8, an ECG is shown as it is sensed from channel 2 (which may correspond to electrode pair 60), with an electrode impedance of 50 ohms and a heart rate of 72 beats. These measurements are derived by the microprocessor 70 from the signals sensed through the sensing electrode pairs, the sensing circuit, and the ECG detection circuit 76. The attendant setting up the defibrillator examines the ECG and other parameters for each channel and based on attendant's observations and experience, the attendant then selects the best or optimal channel by manipulating knob 26.

Next, in step 110, the parameters for a particular therapy are selected by the attendant, including a cardiac rate Rmin. The range of Rmin is about 120–240 BPM. Another parameter set during step 110 is the rate Rmdf. Generally, the rate Rmdf is higher than Rmin.

The defibrillation therapy delivered by defibrillator 10 consists of one or more shocks. More particularly, the defibrillator 10 can be set to deliver a number of sequential shocks, for example, one to nine; each having an energy level in the range of 5 to 360 joules. The interval or delay between shocks can also be set from 10 to 600 seconds in either 5 or 10 second increments. These parameters are all selected in step 110. Moreover, if multiple shocks are used, the energy level and or delay of each shock may be constant or can be separately programmed to predetermined levels.

After the operational parameters of the defibrillator 10 have been set (or programmed) in step 110, the defibrillator proceeds to learn to recognize the ECG of the patient in step 112. During this step, the microprocessor 70 monitors the signals sensed on the channel designated in step 108 for a predetermined time period (for example, 20 seconds). In step 114, a test is performed to determine if the ECG signal recognition was successful. For example, during this period the heart rate is determined from the ECG by determining the time interval between successive R-waves, and compared to the Rmin. In addition the amplitude of the ECG signal is compared to a threshold value (such as 0.7 mv). If the heart rate is found to be below the rate Rmin and the amplitude is found to exceed the threshold then the recognition step is successful. If the recognition process is not successful, then in step 116, a message is displayed to indicate failure and the process is aborted. In step 116 suggestions may also be made to the attendant which may cure the problem. For example, the attendant may be asked to reposition the electrode pairs, and/or select a different sensing channel.

If the learning process is found to be successful, then in step 118, the ECG is shown on the display 24 together with the pertinent parameters and the attendant is requested to verify these parameters. In step 120, the attendant is given the choice of accepting the ECG or to reject it. If the attendant rejects the ECG, the process is aborted. If the attendant accepts the ECG, then in step 122, the attendant is asked to select a mode of operation (i.e., automatic or advisory). In step 124, the choices made during the initialization process are displayed to the attendant. The attendant can request that the selected parameters and mode of operation be printed out during this step.

In step 126, the attendant is given the choice of accepting the parameters as they were set in steps 106–122. If the parameters are accepted, then in step 128, the initialization process is completed, the defibrillator automatically print the parameters, and the operation starts its normal operation mode.

If in step 126, the attendant does not approve the parameters but instead selects to edit them then the process goes back to step 106.

If the attendant decides to cancel the selected parameters (step 130), the process is aborted.

Once the defibrillator 10 has been properly initialized, it is ready for operation. As described above, the mode of operation of the defibrillator 10 is determined by position of the selector switch 28. If this switch is in the auto/advisory position, and it has been previously set to the automatic mode, then it operates as described in the flow chart of FIG. 9. Starting with step 150, the defibrillator first monitors the condition of the patient's heart. During this time, the display 24 is used to show the following information: the mode of operation (in this case AUTOMATIC), the current ECG, the current heart rate Rcur and the selected Rmin.

Figure 9A:
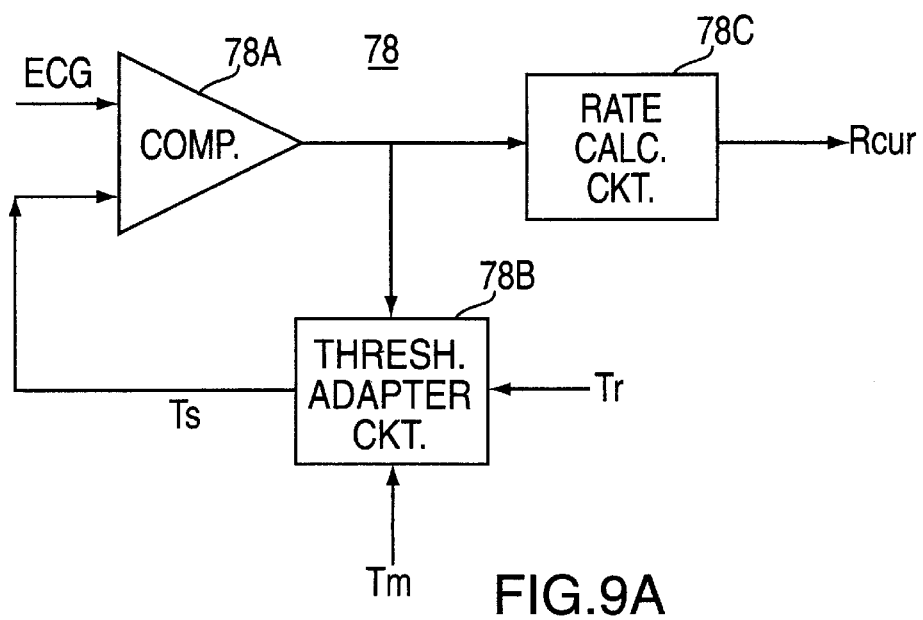
FIG. 9A shows details of a rate detecting circuit for the defibrillator of FIGS. 1–5.
Figure 9B:
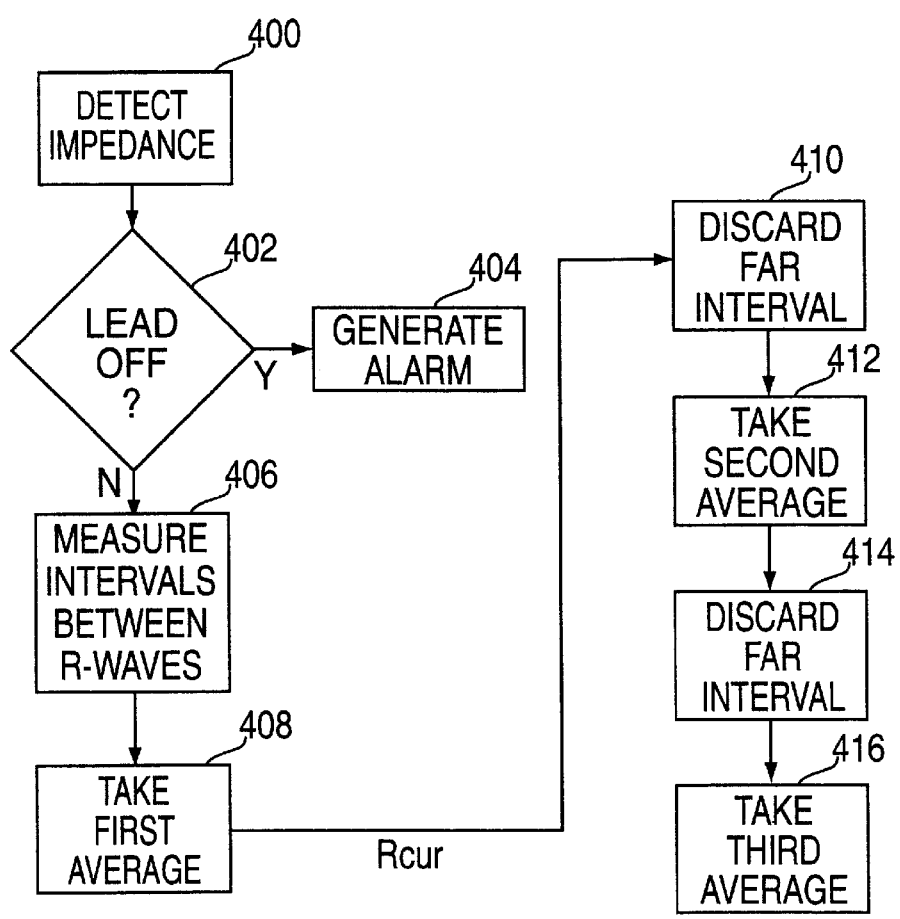
FIG. 9B shows a flow chart for the operation of the circuit of FIG. 5A.

The current heart Rcur is determined using the circuit 78 as shown in FIGS. 9A and 9B. The circuit 78 includes a comparator 78A, a threshold selector circuit 78B and a rate calculator circuit 78C. The comparator 78A and the threshold selector circuit 78B cooperate to detect the intrinsic ventricular rate in an adaptive manner. That is, prior to the acquisition of any signals, the circuit 78B selects a low threshold level Tr which may in the order of 0.2 millivotes. Once a sensed signal exceeding this level is detected by comparator 78A, the signal is identified as a potential R-wave. Thereafter. for a predetermined time period for all future incoming signals, the threshold level is increased slightly until a maximum threshold level Tm is reached. In this manner, a multiple digital signal processing method is used to detect the intrinsic cardiac signals using an adaptive threshold.

Next, the signals detected by comparator 78A are fed to a rate calculator circuit 78C. This circuit also receives a signal indicative of whether the the electrodes currently being used to detect the ECG complex are connected properly. This circuit 78C measures the interval between consecutive signals and generates the corresponding a ventricular rate, using a special averaging technique. This technique from comparable 78A has been selected to eliminate the adverse effects of over-sensing and under-sensing the cardiac signals. More particularly, referring to FIG. 9B in step 400, the impedance signal is detected and analyzed. In step 402, a test is performed to determine if this signal is abnormally high, indicating that a lead (or electrode) is off. If a lead is off, then in step 404, an alarm is generated and the rate calculation process is terminated. As part of step 404, a message is shown on display 24 with instructions to the attendant for correcting the problem.

If, in step 402, it is determined that the electrode impedance is acceptable, then in step 406, N intervals between sequential events from comparator 78A are measured. In step 408, a first average AI1 is taken of the N intervals. In step 410, the absolute difference is determined between the average AI1 and each of the intervals. The interval with the largest difference is discarded.

Next, in step 412, a new average AI2 is generated using the remaining N−1 intervals. In step 414, again, the absolute difference between each of the remaining intervals and the average AI2 is determined and the interval corresponding to the largest difference is discarded. In step 416, an average is taken of the remaining N−2 intervals and this average, or more properly, its inverse, is designated as the current cardiac rate Rcur for the patient's heart. This process (steps 400–416) is repeated for each new electric event from the comparator 78A.

Figure 10:
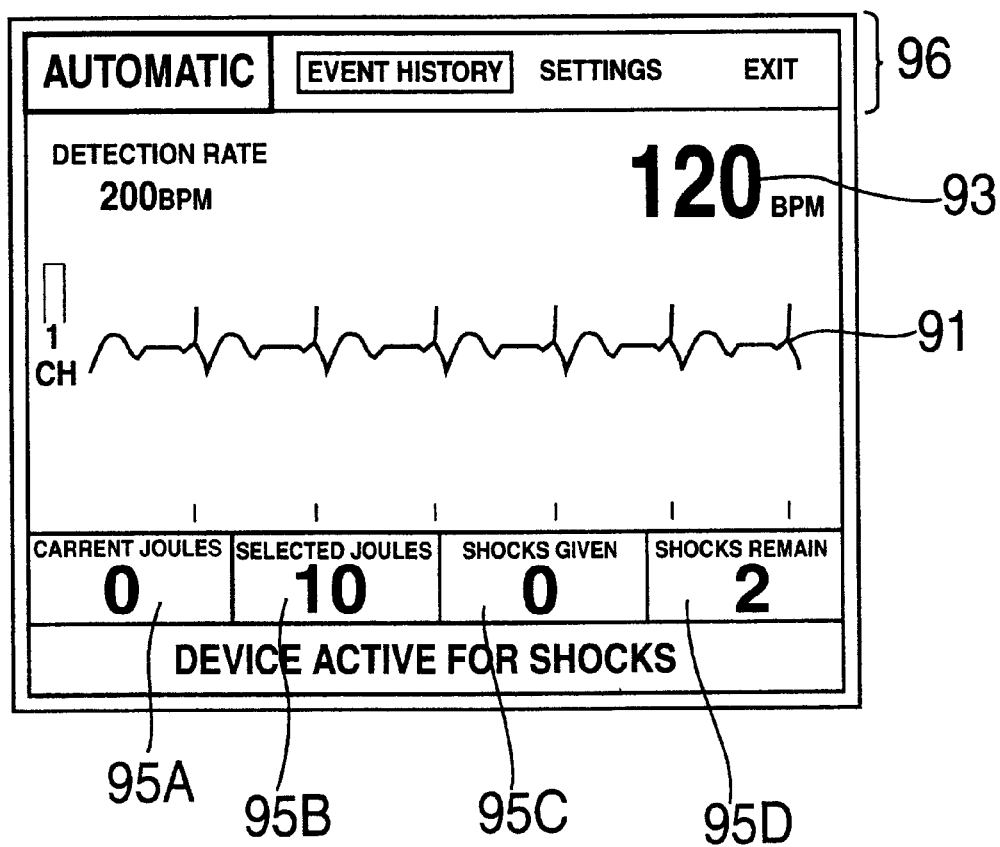
FIG. 10 shows the screen displayed during automatic operation when the defibrillator is ready to apply anti-tachycardia therapy.

Back to FIG. 9, in step 152 at regular intervals, a check is performed to determine if the current rate Rcur (as determined in FIG. 9B) is indicative of a shockable cardiac rhythm is detected. The method of detecting such a shockable rhythm and of determining the corresponding therapy is discussed below, in conjunction with FIG. 14. If a shockable rhythm is detected then in step 154, the arrhythmia is categorized (i.e., as a tachycardia or fibrillation). In step 156, the display 24 is used to show, as indicated in FIG. 10 the current ECG of the patient, at 91, patient's heart rate at 93, and the therapy parameters selected, including the selected energy level, 95A, the number of shocks delivered 95B the total number of shocks programmed 95C and the total number of shocks that remain to be delivered, 95D. Next, in step 158, the defibrillator issues visual and audible warnings to the attendant indicating that the defibrillator is preparing to deliver shocks to the patient and the patient should not be touched. The visual warnings include turning light 33 on (FIG. 1) and the audible signals including voice signals are generated through the speaker (Not shown).

Next, in step 160, the defibrillation pulse generator 84 is activated to start charging its capacitor 84A. As shown in FIG. 10, the display 24 shows during this time the selected or targeted energy level which was set during the initialization mode. The display also shows at 95A the current charge level within the defibrillation pulse generator. As the capacitor within the generator is charged up, this level is increasing, and a beeping signal is emitted to indicate this gradual charging process.

In step 162, the charge level of the capacitor is tested to determine if the set energy level has been reached. If this level has not been reached, the charging process continues.

When the selected charging level is complete, the defibrillator 10 prepares to apply shocks. In step 164, the indicator 34 is lit to indicate that the defibrillator 10 is ready to apply therapy.

At any time during the process described so far, an attendant can disable the automatic or advisory mode by moving the knob 28 to the disarm or energy selection position. In FIG. 9, in step 166, a check is performed to determine if the knob 28 has been shifted to these positions.

If the defibrillator has not been disarmed, then for all shocks, except the first shock of a treatment in step 168, a delay is imposed to conform to the delay programmed between shocks as discussed above. Once the delay is complete in step 170, an attempt is made to synchronize the shock to the ECG. More particularly in step 172, the ECG is analyzed and an attempt is made to detect an R-wave. If an R-wave is detected, then in step 174, a pulse of predetermined duration and energy level is applied to the patient within a predetermined interval, for example 60 milliseconds, after the R-wave.

As step 172 is initiated, a timer (not shown) is also activated. This timer waits for a predetermined time (for example, 2.5 seconds) for synchronization to be achieved. If no synchronization is achieved in that time period, then in step 178, a shock is applied asynchronously.

The defibrillation shock of step 174, 178 is delivered to the patient by the pads 48, 50 (FIG. 4).

After the deliver of the shock in step 180, the heart rate of the patient is determined. If a non-shockable rhythm is detected (step 182), then no more shocks are applied and the heart monitoring is continued in step 150.

If the shockable rhythm continues, then the process of steps 152–180 is repeated thereby delivering the next level of predetermined therapy.

This process continues until all the predetermined number of shocks are delivered, the system returns to step 150 and continues monitoring the patient.

Preferably, after the predetermined number of shocks is delivered, the heart is monitored in step 150 but no other steps are taken even if a shockable rhythm is detected in step 152 unless the therapy sequence resets after a predetermined period of non-shockable has been detected or the defibrillator has been reset.

If the process described above is halted at any time, for example, by turning knob 28 to the disarm or manual position as set forth above in step 166, then the capacitor 84A associated with the defibrillation pulse generator 84 is discharged internally.

In the above description, it was assumed that a ventricular tachyarrhythmia has been detected in step 154. The process may be modified to suit other types of arrhythmias as well. For example, if a fine fibrillation is detected, the steps 170, 172 are omitted since no synchronization may be achieved.

In the automatic mode, when the peak to peak amplitude of ECG signal is greater than a threshold, e.g. 0.2 milli-volts, to ensure a shock is delivered to a shockable condition, the last intervals immediately before the shock is delivered need to be less than the shockable interval corresponding to the Rmin. In this particular application, two intervals immediately prior to the shock are required to be less than the shockable interval.

Figure 11:
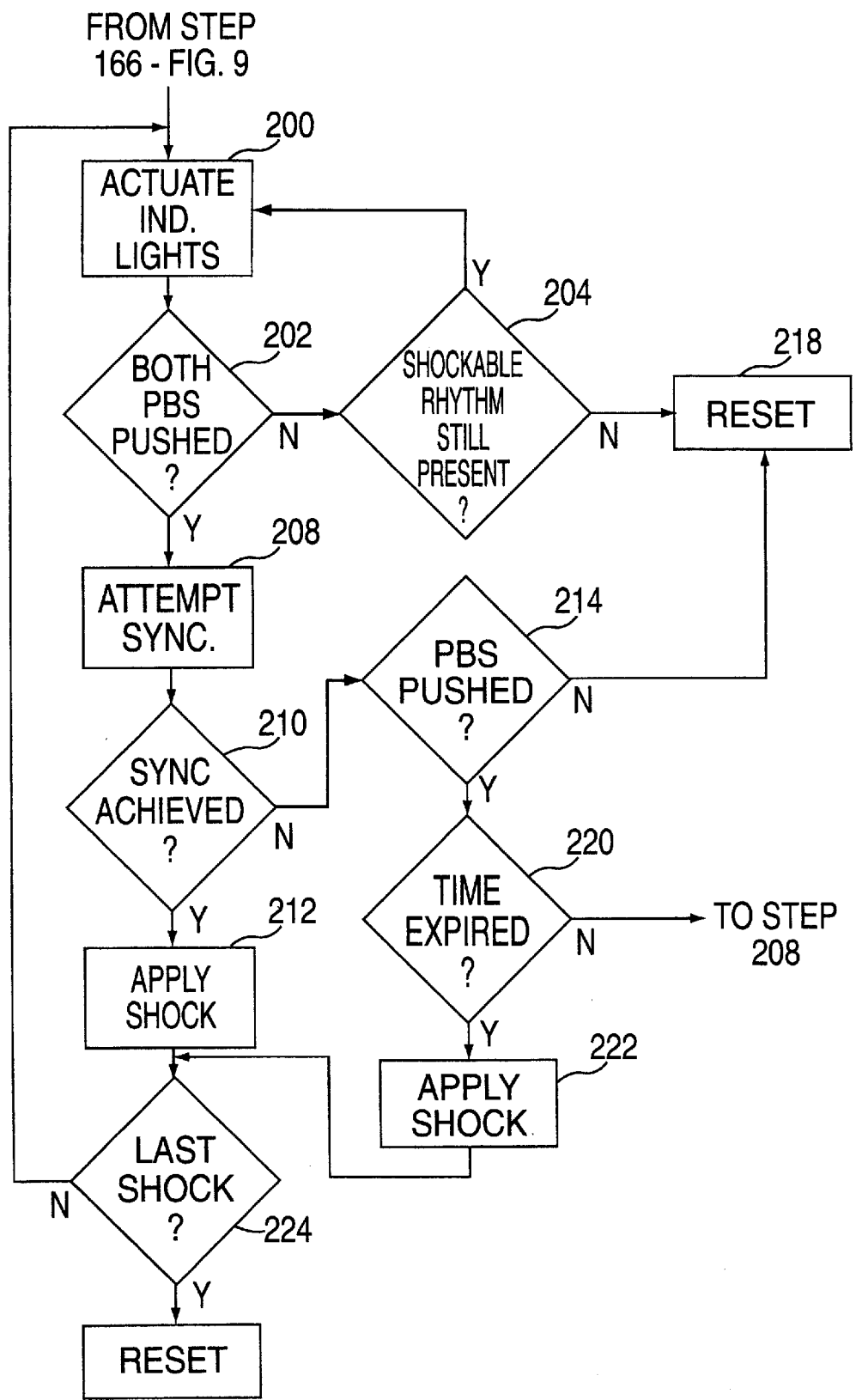
FIG. 11 shows a flow chart illustrating the operation of the device in the advisory mode.

As previously mentioned, one of the operational modes of the defibrillator 10 is an advisory mode. This mode is now described in conjunction with FIG. 11. In this mode the defibrillator performs the same functions that are performed in the automatic mode starting from step 150 through step 166 (FIG. 9). However, after step 166, instead proceeding with the delivery of shock therapy, the lights 30A, 31A associated with pushbuttons 30 and 31 respectively are activated and indicating to an attendant that the defibrillator is ready to apply a shock. The attendant can then elect to apply a shock by depressing pushbuttons 30, 31 simultaneously. A check is performed in step 202 to determine if the pushbuttons have been depressed. If they have not been depressed, then in step 204, a check is performed to determine if the shockable rhythm is still present. If the rhythm is still present, then the lights 30A and 31A remain activated in step 200 and the system continues to wait for the activation of buttons 30, 31. If, in step 204, it is found that a shockable rhythm is no longer present, then the system is reset in step 206.

If the buttons 30, 31 are found activated in step 202, then in step 208, an attempt is made to synchronize with the R wave. In step 210, a check is performed to determine if synchronization was achieved. If synchronization is achieved then a shock is applied in step 212. In step 224, a check is performed to determine if all the prescribed shock pulses have been applied. If shocks still remain, the system returns to step 200. Otherwise, it resets itself.

If no synchronization is achieved in step 210, then in step 214, a check is performed to determine if the pushbuttons 30, 31 are still pressed. If they are not pressed, the system resets in step 216. If the pushbuttons 33, 35 are pressed, then in step 220, a check is performed to determine if a 2.5 second timer has elapsed. If it has not elapsed then the system returns to step 208 and tries to achieve synchronization again. If the timer has elapsed, as indicated in step 220, then in step 222, a shock is applied and the system continues with step 224.

The defibrillator 10 can also be used as a standard manual defibrillator by setting the knob 28 to an energy selection position. In this position, the knob 28 can be used to select the level of energy for the defibrillation shock. In the manual mode, when the pushbutton 92 is activated, the pulse generator 84 charges its capacitor 84A to the level designated by the knob 28. When the desired level is reached, the lights 30A, 31A are illuminated and the shock can be applied by depressing the pushbuttons 30, 31.

An important part of the subject invention is the detection of a shockable rhythm (step 152 in FIG. 9). Primarily, this determination is made from the patient's cardiac rate. When selected, the MDF function is performed by the MDF circuit 80 by analyzing the ECG signal. However, simply setting a rate threshold to detect tachyarrhythmias is insufficient in some cases because an abnormally high rate (above the threshold) may not be ventricular tachycardia origin but from other causes such as sinus tachycardia, SVT (supraventricular tachycardia), or atrial fibrillation. Shock therapy is generally not indicated for these latter arrhythymias and may even be harmful to the patient. In the present invention, the ECG is analyzed and both its magnitude and frequency characteristics are taken into account to distinguish, if possible, VT from other SVT arrhythmias including atrial fibrillation/flutter as well as sinus tachycardia.

More specifically, the present inventors have analyzed and compared the morphologies of VT and SVT rhythms in order to discriminate them. It should be noted that ventricular tachyarrhythmias are characterized by relatively low frequency components, as compared to SVT arrhythmias. Frequency alone may not be adequate for the purposes of this invention. Amplitude must also be taken into account because it fluctuates widely during an arrhythmia episode. However, an amplitude consideration alone (for example, measuring the duration during which the subject wave-shape is above a baseline) has been found to be unsatisfactory because of the inability to detect VT accurately.

Therefore, in the present invention, a procedure has been found which takes both frequency and amplitude into consideration and hence it is referred to as MDF or modulation domain function. The method and apparatus for detecting a shockable event herein has been designed to reduce the probability of delivering therapy for an SVT condition even if its characterized by a rate which is higher than the threshold value Rmin.

Figure 12:
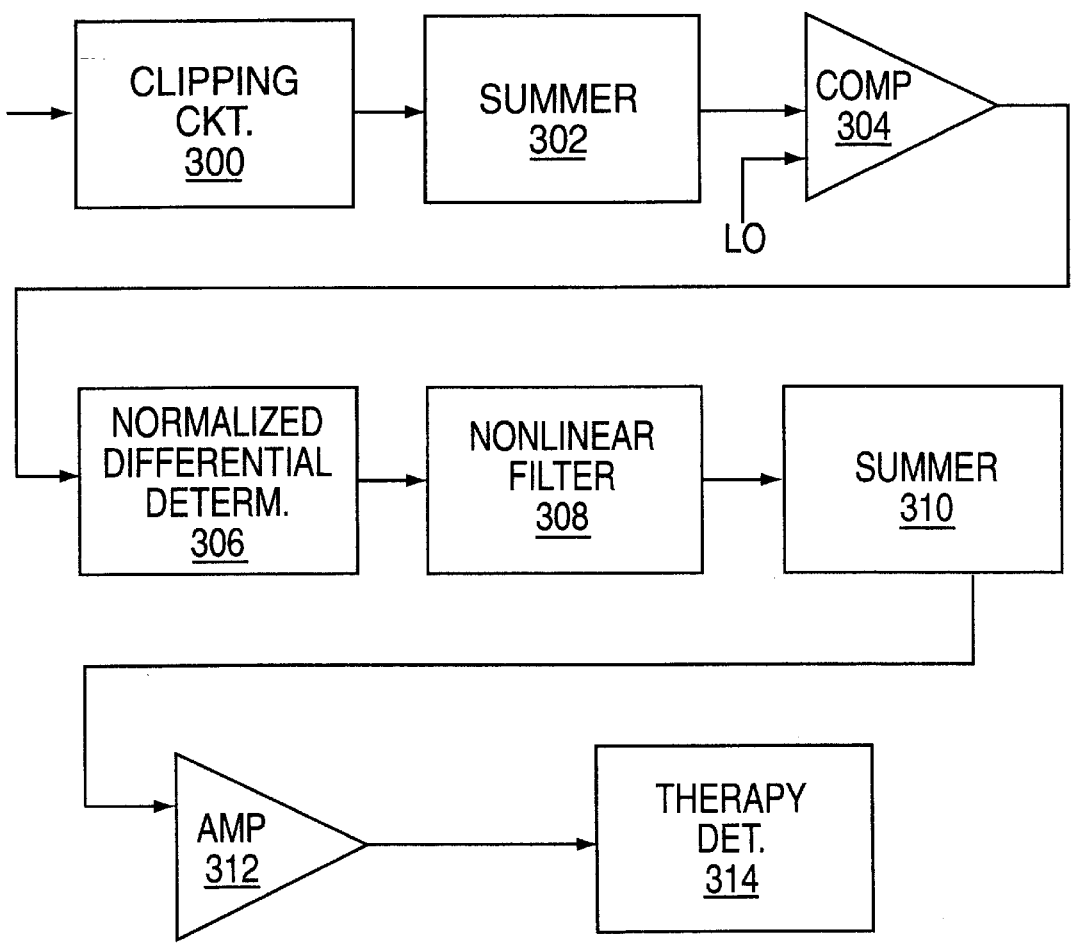
FIG. 12 shows a block diagram for the tachycardia detector circuit of FIG. 5.

Referring now to FIG. 12, the MDFr circuit 80 includes a clipping circuit 300, a first summing circuit 302, a comparator 304, a differential normalizing element 306, a second summer 308, and a comparator 310.

Figure 13:
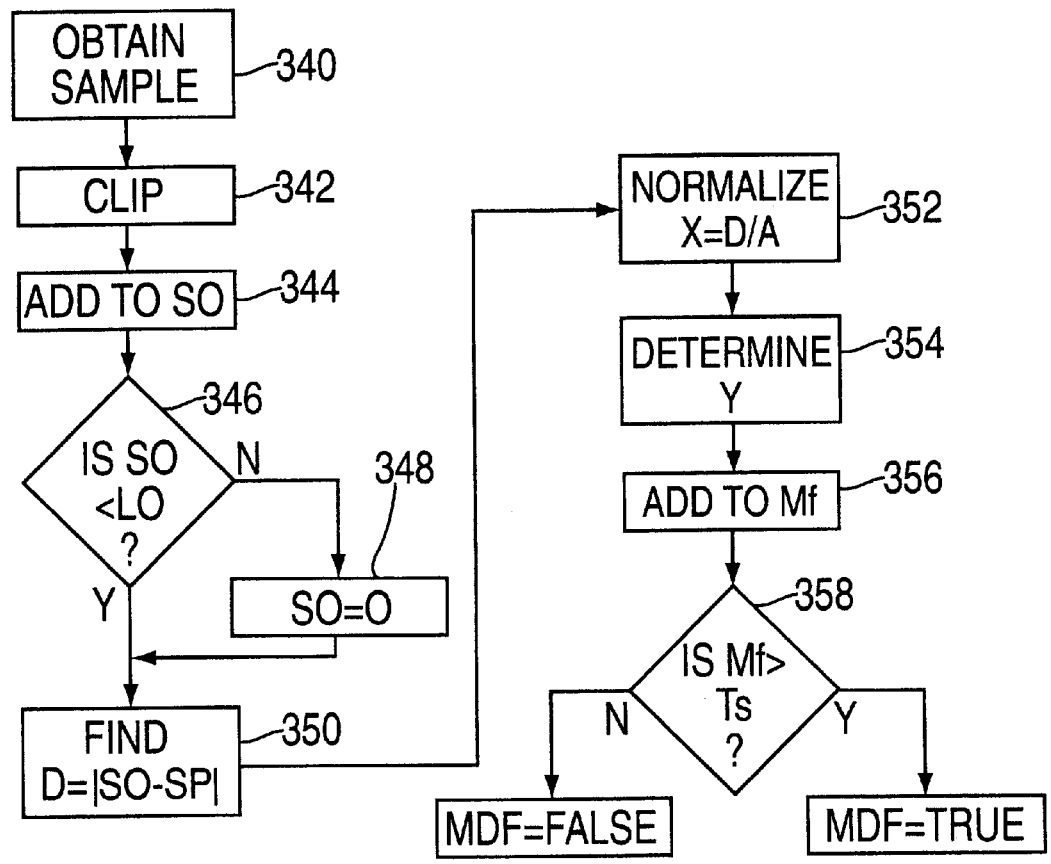
FIG. 13 shows a flow chart illustrating the operation of the circuit of FIG. 12.

The operation of the circuit shown in FIG. 12 will now be described in conjunction with the flow chart of FIG. 13. The circuit 78 receives from circuit 76 a stream of digital signals Ai representative of the current ECG. As each digital signal is received (step 342), it is first clipped by clipping circuit 300 so that it does not exceed a predetermined maximum value (step 302). This step insures that abnormally large values do not unbalance the evaluation performed by the circuit 80. After clipping, the signals Ai are fed to the summer 302. The summer 302 generates a running sum S0 (step 344) of all the digital signals received over the period T. Typically, T may be about 64 milliseconds.

Next, in step 306 the running sum S0 is compared to a threshold value L0 by comparator 304. If S0 is below threshold value L0 then so is set to zero (step 348) to insure that any baseline noise existing in the ECG signal does not contribute to the summation.

Next, a normalized differential parameter X is determined by element 308 as follows. First a differential parameter D is determined using the relation:

$$D=|S0-SP|$$

where S0 is the current sum from summer 302 and SP is the immediate previous sum, i.e., before the current digital signal Ai has been processed by the summer 302. The parameter D is then normalized in step 352 by dividing it by the digital signal Ai to obtain the parameter X (i.e., X=D/Ai). The purpose of this step is to reduce the effect of any sudden amplitude changes in the signals Ai.

The parameter X is then fed to filter 308 which is a non-linear filter that uses four preselected parameters to perform a specific filtering function (step 354) to generate a filtered parameter Y. This parameter Y is related to X as follows:

| X | Y |
|---|---|
| $X \leq B0$ | 0 |
| $B0 < X \leq B1$ | X |
| $B1 < X \leq B2$ | B1 |
| $B2 < X \leq B3$ | $B1*(B3-X)/(B3-B2)$ |
| $B3 < X$ | 0 | where B0<B1<B2<B3. Typical values for these constants may be 10, 50, 160, and 220 respectively.

The parameter Y is fed to the summer 310. The summer 310 in step 356 generates a running sum of all the values of Y received for the last N seconds. For instance, N may be 4 seconds. The resulting parameter Mf is fed to a comparator 312. This comparator 312 which generates a parameter MDFi as follows. In step 356 the parameter Mf is compared to the threshold Ts. If Mf is greater than Ts then the comparator 312 generates an MDFi which is true. Otherwise MDFi is false.

One of the programmable options of the defibrillator 10 is the selective enablement of the MDF circuit 80. That is, during the initialization of the defibrillator 10, the attendant has the choice of activating the circuit 80, in which care the parameter MDFi is determined as described above, or the function can be disabled, in which care the MDFi is ignored.

Referring back to FIG. 5, the parameter MDFi is fed to the therapy selector 82. This selector 82 monitors the current cardiac rate Rcur and parameter MDFi (if applicable) and determines whether therapy is required, and if so, then what kind of therapy should be applied.

Figure 14:
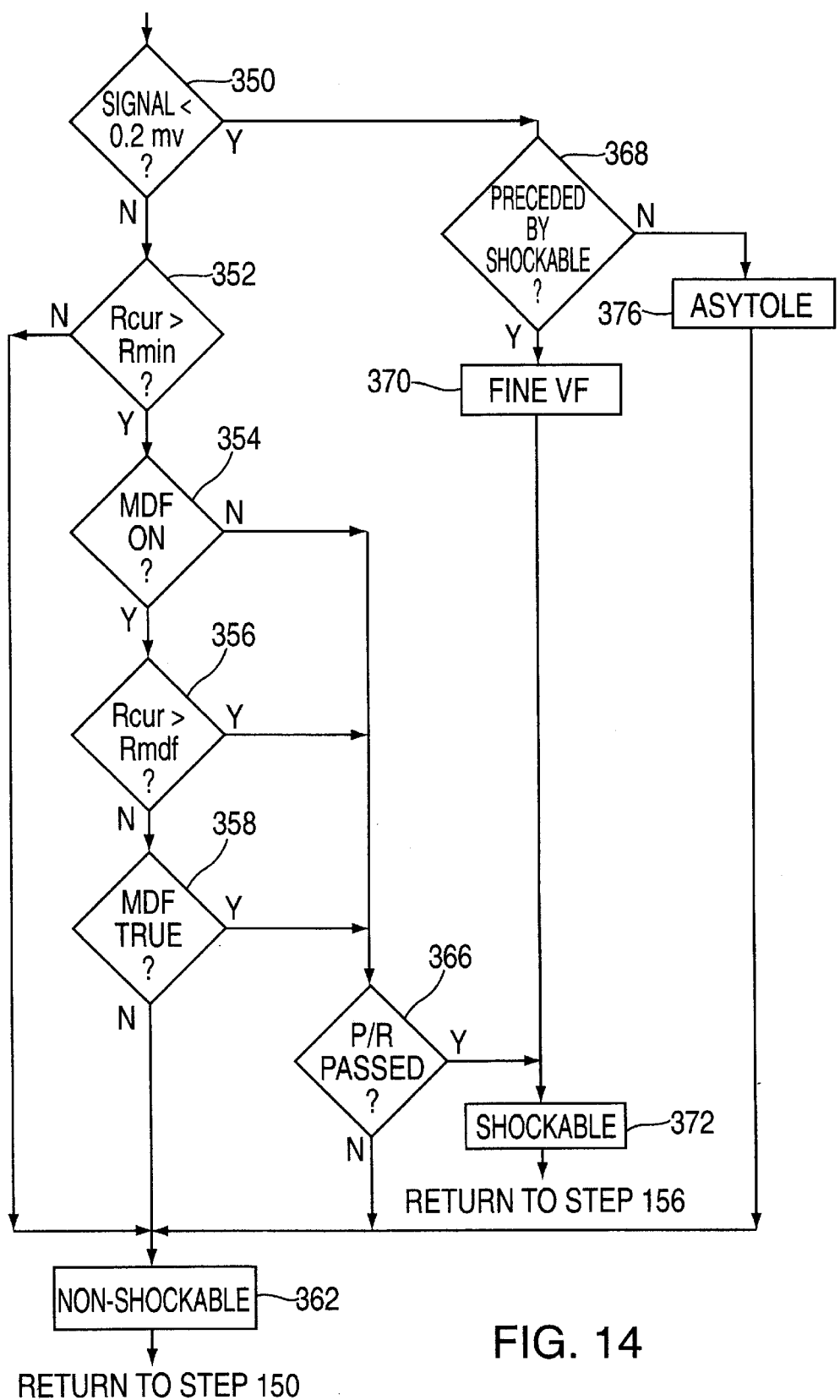
FIG. 14 shows a flowchart illustrating the operation of the therapy selector of FIG. 5.

Referring to FIG. 14, in step 350, a check is performed from step 150 to determine if the peak to peak amplitude of the signal is less than 0.2 milli-volts for the previous seconds. If it does, the algorithm checks to see if a shockable rhythm has been detected prior to this latter period 368. If a shockable rhythm has been detected, the algorithm classifies the rhythm as Fine VF 370 which is shockable 372. If a shockable rhythm has not been detected, the algorithm classifies the rhythm as a systole 376 which is not considered a shockable rhythm 362.

Referring to FIG. 14, in step 352, the current rate Rcur from step 350 is first checked to see if it exceeds the minimum rate Rmin. If it does not, then the rhythm is classified as non-shockable 362 and monitoring of the heart continues in step 150 without any therapy. In step 354, a check is performed to determine if the MDF mode has been activated. If it is not, it continues to step 366. If this mode has been activated in step 354, a check is performed to determine if Rcur is greater than Rmdf 356. If it is, it continues to step 366. In step 358, a check is performed to determine if the parameter MDFi is true. If it is true, it continues to step 366. If MDFi is not true, the rhythm is classified as non-shockable 362 and no therapy is performed at this time. In step 366, a P of R test is performed during which P of the last R intervals must have corresponded to a rate higher than Rmin. For example, P could be 4 and R could be 6. If the test failed, the rhythm is classified as non-shockable 362, and it returns to step 150.

If the P of R test is passed, then the current rate Rcur is designated as a shockable rhythm corresponding to ventricular tachyarrhytbmias and the process continues to step 156 in FIG. 9.

In summary, the microprocessor 70, rate detector 78, and MDF circuit 80 and the therapy selector 82 cooperate to determine if the current cardiac condition of the patient should be classified as a shockable rhythm or not based on the current rate Rcur as well as the amplitude and frequency of the ECG signals. If the rate Rcur is below the threshold Rmin, no therapy is applied. If the rate is above Rmin, a determination is made as to whether the rhythm is shockable or not, based the parameters and modes described. Since VT and ventricular fibrillation could be life-threatening, it is preferably that a conservative approach be taken when selecting these parameters.

The process and apparatus described above and in FIGS. 12 and 13 is primarily designed for use in the automatic external cardioverter/defibrillator, however it may also be used in internal defibrillator/cardioverter devices and other cardiac devices as well.

Obviously, numerous modifications may be made to this invention without departing from its scope as defined in the appended claims.

We claim:

1. An external defibrillator that can be used to apply therapy to a patient, comprising:
    an electrode adapted to couple externally to the body of a patient;
    a sense circuit coupled to said electrode to sense a physiological signal of the patient indicative of intrinsic cardiac activity;
    a cardiac arrhythmia detector coupled to said sense circuit to detect an abnormal cardiac arrhythmia based on said physiological signal, said cardiac detector including a rate detector adapted to detect an intrinsic cardiac rate, said rate detector including an averaging element for averaging the intrinsic rate over several cardiac cycles to generate an average rate parameter, said averaging element includes a rate calculator adapted to determine a first average for a Predetermined number of cardiac events, said rate calculator being further adapted to determine a second average by dropping measurements related to one of said events, said second average being related to said cardiac rate, said abnormal cardiac arrhythmia being detected by using said average rate parameter;
    a microprocessor-based controller adapted to generate automatically a command in the presence of said cardiac arrhythmia; and
    a therapy delivery circuit adapted to deliver electrical therapy pulses to said patient to correct said abnormal cardiac arrhythmia in response to said command.

2. The defibrillator of claim 1 wherein said cardiac arrhythmia detector includes a comparator adapted to compare said physiological signal to a threshold value to identify a cardiac event used to determine said cardiac rate.

3. The defibrillator of claim 1 wherein said rate calculator is further adapted to determine a third average by dropping measurements associated with another of said events.

4. The defibrillator of claim 1 wherein said cardiac arrhythmia detector includes a descriminator that descriminates between ventricular tachycardia, fine fibrillation and a systole, and wherein said therapy delivery circuit is adapted to deliver cardiac therapy appropriate for the condition indicated by the descriminator.

5. The defibrillator of claim 1 wherein a difference is determined between each of said measurements and said first average, the largest of said differences is determined and the event corresponding to said largest difference is dropped.

6. An external defibrillator for generating cardiac therapy for a person suffering from an abnormal cardiac condition, said external defibrillator comprising:
    a first electrode adapted to be attached to said patient;
    a detector circuit coupled to said first electrode and adapted to detect an abnormal cardiac condition based on a physiological signal sensed through said first electrode, said detector circuit detecting a cardiac rate based on predetermined number of cardiac events and omitting some of said events based on predetermined criteria to avoid over- and under-sensing;
    a microprocessor-based controller coupled to said detector circuit and adapted to generate a command in the presence of said life threatening condition; and
    a pulse generator adapted to generate therapeutic pulses selected to terminate said abnormal cardiac condition in response to said command.

7. The external defibrillator of claim 6 further comprising a second electrode attached to said patient and being coupled to said pulse generator to deliver said therapeutic pulses to the patient's heart.

8. The external defibrillator of claim 7 wherein said second electrode is coupled to said pulse generator to deliver said therapeutic pulses to the patient's heart.

9. The external defibrillator of claim 6 further comprising a sensor circuit coupled to said first electrode to sense intrinsic cardiac signals, said sensor circuit being adapted to transmit said intrinsic cardiac signals to said detector circuit.

10. The external defibrillator of claim 6 further comprising a self-test and diagnostic circuit adapted to run tests on said external defibrillator to determine if said external defibrillator is operational.

11. The external defibrillator of claim 6 wherein said detector circuit is adapted to detect intrinsic cardiac signals and said controller is adapted to generate said command in synchronism with said intrinsic cardiac signals.

12. The external defibrillator of claim 11 wherein said detector circuit is adapted to detect R-waves and said controller is adapted to generate said command at a predetermined interval after said R-waves.

13. The external defibrillator of claim 12 wherein said controller is adapted to delay said command after said R-wave.

14. The defibrillator of claim 6 wherein said detector circuit includes a comparator adapted to compare said physiological signal to a threshold value to identify a cardiac event used to determine said cardiac rate.

15. The defibrillator of claim 14 wherein averaging element includes a rate calculator adapted to determine a first average for a predetermined number of cardiac events, said rate calculator being further adapted to determine a second average by dropping measurements related to one of said events, said second average being related to said cardiac rate.

16. The defibrillator of claim 15 wherein said rate calculator is further adapted to determine a third average by dropping measurements associated with another of said events.

17. The defibrillator of claim 16 wherein said cardiac arrhythmia detector includes a descriminator that descriminates between ventricular tachycardia, fine fibrillation and asystole, and wherein said therapy delivery circuit is adapted to deliver cardiac therapy appropriate for the condition indicated by the descriminator.

18. The defibrillator of claim 6 wherein said controller is adapted to operate in one of an automatic and an advisory mode selectable by an attendant, wherein in said automatic mode, the controller generates commands and said pulse generator applies shocks responsive to said commands without any signals from the attendant and wherein in said advisory mode said controller generates commands and said pulse generator applies shocks responsive to signals from the attendant.

19. The defibrillator of claim 6 wherein said controller is adapted to operate in one of an automatic and a advisory mode selectable by an attendant, wherein in said automatic mode, the controller generates commands and said pulse generator applies shocks responsive to said commands and in accordance with a set of therapy parameters previously set and without any signals from the attendant and wherein in said advisory mode said pulse generator prepares shocks in accordance with selected therapy parameters set by the attendant and shocks prompted to and delivered by the attendant.

20. The external defibrillator of claim 6 further comprising a display, wherein said controller is adapted to provide on said display at least one of an instruction for the operation of the defibrillator and information indicative of a condition of the patient.

21. The external defibrillator of claim 6 further comprising a second electrode adapted to deliver said therapeutic pulses to the patient and a connector coupled to said first and second electrodes.

22. The external defibrillator of claim 21 further comprising a housing that holds said detector circuit and said pulse generator, and a cable coupling said connector to said housing.

23. A method of providing cardiac therapy to a patient suffering from a life threatening cardiac condition using an external defibrillator having an electrode, said method comprising the steps of:
attaching said electrode to the patient to sense a physiological signal indicative of intrinsic cardiac signals;
detecting an abnormal cardiac condition based on said physiological condition by detecting a plurality of cardiac events, measuring a characteristic of said events and averaging said characteristics; and
applying automatically therapeutic pulses in response to said abnormal cardiac condition to said patient;
wherein said step of detecting includes detecting a plurality of intrinsic QRS complexes and measuring the intervals between successive QRS complexes; averaging said intervals to determine a first average related to a cardiac rate; determining the differentials between said average and the intervals between each QRS complex, and then determining a second average by dropping the QRS interval with the largest differential, said second average being indicative of said abnormal cardiac condition.

24. The method of claim 23 further comprising determining the differentials between said second average and the remaining intervals and then determining a third average by dropping the interval with the largest differential.

25. The method of claim 23 wherein said external defibrillator includes a display, further comprising providing on said display instructions for the operation of the defibrillator.

26. The method of claim 23 wherein said therapeutic pulses are applied to the patient with said electrode.

27. The method of claim 23 wherein said external defibrillator includes another electrode and wherein said therapeutic pulses are applied to the patient through said another electrode.

28. The method of claim 23 wherein an abnormal cardiac rhythm is detected and wherein the heart rate reverts to a normal sinus rhythm without the application of therapy, comprising aborting the application of any therapy.

29. The method of claim 23 wherein after said abnormal cardiac rhythm is detected and therapy is applied causing the heart rate to revert to a normal sinus rhythm wherein, the application of further therapy is aborted.

30. The method of claim 29 further comprising monitoring the heart for another abnormal cardiac rhythm after said reversion.

31. The method of claim 23 further comprising checking whether a predetermined number of cardiac intervals are smaller than an interval corresponding to a threshold rate Rmin immediately prior to the application of a therapeutic shock.

32. The method of claim of claim 23 further comprising checking an electrical characteristic associated with said electrode prior to the application of a therapeutic shock, wherein said therapeutic shock is applied only if said characteristic meets a predetermined criteria.

33. The method of claim 32 wherein said step of checking includes measuring an electrode impedance and determining if said impedance is in the range of 15–200 ohms.

34. The method of claim 23 further comprising selectively applying therapy to the patient in a manual mode comprising:
selecting an energy level by an attendant;
charging the defibrillator to the selected energy level; and
manually initiating a command and to discharge said defibrillator.

* * * * *